United States Patent
Williams et al.

(10) Patent No.: US 7,250,871 B2
(45) Date of Patent: Jul. 31, 2007

(54) PARTICULATE DETECTOR

(75) Inventors: Leonard Frederick George Williams, Buckingham (GB); John Richard Bann, Derbyshire (GB); Nigel Edward Harris, Derbyshire (GB); Jeremy Francis Siddons, Derbyshire (GB)

(73) Assignee: Unidata Europe Limited, Sheffield (GB)

( * ) Notice: Subject to any disclaimer, the term of this patent is extended or adjusted under 35 U.S.C. 154(b) by 269 days.

(21) Appl. No.: 10/956,335

(22) Filed: Oct. 4, 2004

(65) Prior Publication Data

US 2005/0259255 A1 Nov. 24, 2005

(30) Foreign Application Priority Data

Oct. 2, 2003 (GB) .................. 0323055.4

(51) Int. Cl.
*G08B 21/00* (2006.01)
(52) U.S. Cl. ................... 340/627; 340/630; 340/632
(58) Field of Classification Search ........... 340/632, 340/633, 634, 627, 628, 629, 630; 250/356.1, 250/339.1; 355/30, 53; 356/337, 311, 343
See application file for complete search history.

(56) References Cited

U.S. PATENT DOCUMENTS

| | | | | |
|---|---|---|---|---|
| 4,228,353 A | * | 10/1980 | Johnson ................ 250/356.1 |
| 4,711,571 A | * | 12/1987 | Schuman ................ 356/311 |
| 4,786,817 A | * | 11/1988 | Boissevain et al. ..... 250/559.01 |
| 4,801,352 A | * | 1/1989 | Piwczyk ................ 156/345.5 |
| 6,055,052 A | | 4/2000 | Lilienfeld ............... 356/338 |
| 6,476,911 B1 | * | 11/2002 | Rose ..................... 356/337 |
| 6,731,371 B1 | * | 5/2004 | Shiraishi ................. 355/30 |
| 2002/0105645 A1 | | 8/2002 | Eriksson | |

FOREIGN PATENT DOCUMENTS

WO    WO 03/012375 A3    2/2003

\* cited by examiner

*Primary Examiner*—Van T. Trieu
(74) *Attorney, Agent, or Firm*—Squire, Sanders & Dempsey L.L.P.

(57) ABSTRACT

An apparatus and method are provided for detecting presence in gas of transient particulate above its normal zero or acceptable level within a duct (4), said apparatus comprising at least one emitter (2) of illumination selected from infrared, ultraviolet and visible radiation capable of being projected over essentially the entire cross section of the duct (4) and at least one detector (8, 18, 25) for detecting any sparkle of the illumination from the particulate. The apparatus and method are in particular useful for detecting monitoring particulate in areas where build up or presence of particulate can be disadvantageous, for example hospitals and electricity generating stations.

30 Claims, 7 Drawing Sheets

Laser projecting
plane of illumination

Camera with view
of entire plane of illumination (a)

(b)

(a)

(b)

PARTICULATE DETECTOR

FIELD OF THE INVENTION

This invention relates to particulate detection and in particular to apparatus and methods for the detection, including monitoring of particulate.

BACKGROUND OF THE INVENTION

The presence of particulate is in many situations at least a nuisance and at worst catastrophic or illegal. Particulate can carry impurities into locations where its presence is undesirable. Such locations include industrial plant and the environment including air quality monitoring. Thus in the manufacture for example of electronic components the presence of particulate can lead to impurities being included inadvertently in the component, for example, a chip, so rendering the component faulty. Many testing procedures are carried out in areas which are intended to be sterile and particulate free; the presence of particulate may lead to test results from such contaminated areas worthless. In a hospital environment, for example, it is necessary that many wards and, in particular, operating theatres, be kept essentially particulate free so that conditions be maintained as sterile as possible. In electricity generating stations, for example, particulate in the inlets to turbines must be kept to a minimum in order to reduce particulate build up on the turbine blades; such build up has to be removed, generally by water spraying, or, if not carried out, leads to a reduction in turbine performance and ultimately blade disintegration with obvious destructive results. In either event, generating time is reduced.

Particulate free conditions in the examples given above should exist in the inlet of gas, often air, into the relevant area. However particulate should not be fed through the outlet of an area. For example, exhaust from power stations, industrial processing including chemical plant processes, should not emit particulate into the atmosphere. Such a practice is environmentally unacceptable and particulate emissions must be kept within approved maximum or legal limits.

Particulate entering or leaving an area is generally reduced by the use of a range of abatement systems, often located in a duct through which gas is supplied to an area or removed from an area. Such abatement systems include, for example, filters, combination of filters, electrostatic precipitators, wet arresters. If the abatement system has been fitted incorrectly or erroneously or in time the abatement system degrades, the efficiency of the abatement system in reducing particulate passing through the abatement system is reduced. It is common practice to replace an abatement system after a given period which is determined by experience, of acceptable abatement system performance. It is also found however that an abatement system may fail catastrophically before that period has been exhausted and allow unacceptable passage of particulate through the filter system. This is a particular problem where, for example, the gas flow is very high or where the abatement system comprises a set of filters and one filter in the set should prematurely fail.

Presently available particulate detectors only detect the presence of particulate in a very narrow band or area in a duct. In one such detector, a conductive rod is located in a duct and any increase in charge caused by charged particulate passing close to or striking the rod induces a current in the rod which is detected. Such a detector measures particulate over a very small volume of the duct and the rod acts as an obstruction to gas flow in the duct. In another detector, a very narrow, pencil like beam of light is directed across the duct and opacity measured over a single cross duct measurement is made. In yet another detector, a very narrow beam is projected into a duct and a detector is focussed on a small portion of the beam, typically 15 cm, and reflection back from the portion of the beam monitored. All these detectors measure presence of particulate over a very small cross sectional area of a duct and presence of particulate over more of the cross section can only be estimated by extrapolation and are wholly reliant on the assumption that turbulence is present, which causes an even distribution of particulate across the cross sectional area of the duct which is not always the case, especially where true laminar flow exists.

There is therefore a requirement for an apparatus and a method for detecting of particulate suspended in gas in such ducts over the cross section of the duct. Detecting of particulate on a regular basis also leads to continuous or regular monitoring of a duct so as to detect the presence of transient particulate above its normal zero or low acceptable level and the apparatus of the invention provides such a facility. In these ducts, the normal level of particulate is essentially zero (i.e. particulate free) or at a very low and acceptable level when the abatement system is performing efficiently. The apparatus of the invention avoids an assumption that a small sample of the cross section represents the whole of the cross section Other detectors are known such as those described in PCT Application 03/012375 where quantitative measurement of large concentrations of particulate in a gas environment are to be determined, preferably by microwave technology, in pipework; however such detectors, and those in the patent publication and patent specification described below, only sample selected cross sectional portions of the pipework and assume approximate homogeneity of particulate concentration therefrom. Accordingly such a detector does not function where such approximate homogeneity does not exist. Furthermore, such a detector does not provide monitoring of low levels of particulate. In U.S. patent publication 2002/0105645 A1 there is described an apparatus for monitoring particulate in water or oil; however the apparatus provides only point to point measurement in pipework. The apparatus of U.S. patent specification No. 6,055,052 measures particle size, and not unexpected presence of particulate in air within pipework. The problem solved and information gathered from the apparatus of the foregoing patent specifications are wholly different from the problem to be solved by the apparatus and method of the present invention.

SUMMARY OF THE INVENTION

According to the present invention an apparatus is provided for detecting presence of transient particulate in gas within a duct comprises at least one emitter of illumination selected from infra red, ultra violet and visible radiation capable of being projected over essentially the entire cross section of the duct and at least one detector for detecting any sparkle of the illumination from the particulate.

According to a further aspect of the present invention an apparatus is provided for detecting presence of transient particulate in gas within a duct comprises a duct and at least one emitter of illumination selected from infra red, ultra violet and visible radiation capable of being projected over essentially the entire cross section of the duct and at least one detector for detecting any sparkle of the illumination from the particulate.

According to a further aspect of the present invention a method is provided for detecting particulate in gas within a duct which comprises subjecting a duct with at least one emitter of illumination selected from infra-red, ultraviolet and visible radiation, projecting the illumination over a substantial cross section of the duct and detecting any sparkle of the illumination from the particulate.

The apparatus and method of the invention are useful therefore in detecting the presence of transient particulate in gas in the inlet or outlet of an industrial process, suitably after the gas has passed through an abatement system, and in particular upstream in an inlet or downstream in an outlet of that process, e.g. before or after respectively, of e.g. a turbine.

By the term "essentially the entire" in respect of the cross section of a duct is meant that sufficient of the cross section of the duct is illuminated so that sampling of selected cross sectional portions of the pipework and assumption of approximate homogeneity of particulate concentration are not required and therefore the invention provides accurate and actual detection of the presence of particulate over the whole cross section of the duct is obtained. The term "essentially the entire" preferably requires that the whole of the cross section of the duct is illuminated but a few voids may be tolerated, for example, not more that 10% of the cross section of the duct.

By the term "substantial cross section" in this specification is meant that at least 10%, preferably 50%, highly preferably 80% of the, and most preferably essentially the entire, cross section of the duct is covered by illumination from the emitter.

By the term "particulate" in this specification is meant animal, vegetable or mineral material in particle form. In particular the term includes minute particulate material found in the atmosphere and generated within industrial processes and engines. The term "gas" in this specification is meant any gaseous material, in particular air, which does not react chemically with material used in the abatement system.

The apparatus and method of the present invention rely on the detection of sparkle from particulate of illumination to which they are subjected. By the term "sparkle" is meant glitter or glisten of illumination from a particulate. The sparkle may be in any direction as illumination is reflected from the particulate; at least some of the sparkle will be in the direction of the detector. In an area of gas flow, the apparatus of the invention, and its method, enable more accurate determination of particulate suspended in the gas flow over substantially the whole cross section of the duct. If gas close to the outlet of a filter is essentially laminar, it is preferred that the apparatus of the invention is located in the area of laminar flow. Such positioning will enable more precise determination of the location of a fault in a particular filter in a planar array of filters.

The apparatus of the invention will be located within an inlet or outlet duct which directs gas into or out from a location. The duct may be constructed from any suitable material known in the art. Examples of ducting include metal, typically, steel which may be coated or uncoated (e.g. galvanised), stainless steel, aluminium; plastics materials, for example rigid or flexible polyvinyl chloride, polypropylene, polystyrene, low or high density polyethylene, ABS and the like; and the ducting may be in concertina form. The ducting may be of any convenient or suitable cross section such as, for example, rectangular (e.g. square), circular, oval, and have any cross sectional size provided that the cross section can accommodate the emitter and detector. The emitter and/or the detector may be located within the cross section of the ducting; however, where there is very high throughput of gas, the emitter and the detector are preferably located in the wall of the ducting or adjacent a window (transparent to the illumination) in the ducting wall so that the emitter or detector do not reduce throughput of gas and the risk of any part of the emitter or detector being dislodged and damaging the duct or apparatus is reduced.

The illumination is selected from infrared, ultra violet and visible radiation which is capable of producing sparkle from particulate. It is preferred that the illumination is in the visible spectrum.

Infra red illumination, which has lower costs than other emitters described below may be used and whilst any water vapour present in the duct or gas will absorb at least some of the infra red illumination, such disadvantage may be alleviated by use of detectors such as, for example CCD cameras (which have a peak sensitivity at about 675 nm) which are sensitive in an area of low absorption in the infra-red spectrum of water; however illumination intensity is comparatively low (which may be compensated for by increasing sensitivity of detectors) and poor collimation and longer wavelength may limit detectability of sparkle.

Ultra violet illumination may also be used but comparatively high cost and low sensitivity of the detector are disadvantages.

Microwave illumination is not a suitable source of radiation because vibrations in the duct and external movements to the duct cause vibrations which render any detection of sparkle unreliable. Also commercially available microwave systems rely on Doppler Shift for detection of particulates which is a different effect from that required in the present invention; Doppler Shift measures speed of particles and hence microwave systems provide little back scatter or sparkle. Furthermore, the wavelength of microwave illumination is very large compared to the normal dimensions of individual particulate particles, bulk reflection of microwave illumination occurs from clouds of particulate. Beam size and direction are relatively easily controllable and so give adequate control of coverage of the duct, but multipathing is a problem associated with microwave radiation. Also transparency of materials from which the duct is made can result in unwanted signals.

Illumination in the visible spectrum is preferred. Illumination having wavelength from 460 nm to 680 nm is preferred. Emitters of visible illumination include that, for example, from a filament lamp, light emitting diode, but such light generally may not have adequate intensity or be capable of being focussed to provide a beam having required collimated beam. A much preferred emitter is a laser. It has been found that lasers produce intense sparkle from particulate and laser devices have comparatively longer operating life. Suitable lasers have output of at least 1 mW, and output may be determined having regard to particulate size and required sensitivity of the apparatus. Matching of a single frequency emitter with a detector specific for that frequency results in greater signal to noise ratio in detection and hence greater sensitivity of the apparatus of the invention. The duct may be provided with a beam dump to absorb illumination, in particular illumination from a laser, on the side of the duct opposite to the emitter so that illumination is not reflected back from the opposite side of the duct. A band pass filter may also be provided to reduce any effect of non-emitter emitted illumination.

The emitter may be arranged to project illumination across the whole cross section or only one axis of the duct; it may scan by use, for example, of a lens, mirror or of a prism, which may be moved or rotated by a motor by continuous or essentially continuous stepped movement. The emission, suitably from a laser, may be fanned across the duct by use of a line generator. By the term "fanning" is meant that the beam of emitted illumination is spread across the area to be investigated. Whilst it is preferred to use a single emitter of illumination, a plurality may be used, in particular where the cross sectional geometry of the duct is irregular, or the duct structure is not regular.

Fanning of the beam from the emitter by means of, for example, a optical lens, preferably cylindrical, converts a narrow beam into a fan having any desired inclusive angle, preferably about 90°. Such fanning has advantages of low cost, no moving parts and hence requiring little setting-up or alignment; however the intensity of the illumination diminishes rapidly as distance from the emitter increases due to large (and deliberate) divergence of the beam, power is spread over a large area so that emitter output increase is required for any given detector sensitivity, and a 2-dimensional detector is required to monitor sparkles occurring within the whole of the fan. Mechanical scanning of the beam from the emitter by means of, for example, a lens or an essentially continuous mechanically moved mirror enables the beam to be swept through a desired scan angle. Typically a mirror is controlled with a servo galvanometer or a stepper motor, the latter being preferred where mechanical robustness of the apparatus is required; an additional advantage of a stepper motor is that information relating to the position of the emitter beam can be used to mask out any spurious signal. The advantages of such a system enable a constant intensity along the length of the beam (excluding any absorption), maintain high intensity i.e. little spreading of the beam other than normal divergence, and scanning parameters such as sweep angle and sweep rate can be easily controlled. The sweep duration may be from tens of sweeps per second to a few minutes; longer sweep times allow for very sensitive detection of small particulate trails, and small sparkles detection can be integrated over a period of seconds to facilitate measurements of particulate of greater reliability and reproducibility; faster sweep rates generally allow quicker remedial action in the event of catastrophic abatement system failure.

The detector may be any suitable detector that is capable of detecting sparkle of illumination from particulate. Suitable detectors include for example, cameras, phototransistors and pin diodes. A suitable camera may have a sensitivity in the range 0.003 to 1.0 Lux. The detector may be fitted with an optical filter or filters so that, for example, a filter may render a camera sensitive to a narrow wavelength of illumination, and/or a graduated neutral density filter which may be used to aid normalisation of close sparkles and far sparkles. Preferably a single detector or phototransistor may be provided but a plurality of detectors is not excluded.

The relative positioning of the emitter and detector may be optimised and dependent upon the type of detector used. For example, it is preferable for the camera field of view to be offset from the line of direction of the emitter so enabling a two dimensional picture of the illuminated plane to be obtained. However if a detector is located adjacent the emitter so that a beam is sent across the duct, the sparkle detected will be that reflected back (back scatter); however positional information regarding the particulate could not be determined.

Thus in accordance with use of the apparatus and method of the present invention, as particulate pass through the, for example, laser light, a small flash of light reflected back, i.e. sparkle, is detected by one or more of the detectors. Although the amplitude of the sparkle will differ for each dust particle because of differences in particle size and reflectivity, (and also any dirt on the optics), the rate and duration of the sparkles can be used to determine particulate flow and particulate content. Therefore the rate and duration of sparkles may be logged, and the amplitude of the light sparkled may be an indication of particulate intensity. The rate and duration of the sparkles may then be recorded by for example, summation, so as to give an indication of the amount of particulate in the duct.

BRIEF DESCRIPTION OF THE DRAWINGS

The invention is illustrated with reference to the accompanying figures and examples in which.

DESCRIPTION OF THE PREFERRED EMBODIMENTS

EXAMPLE 1

Figure 1:
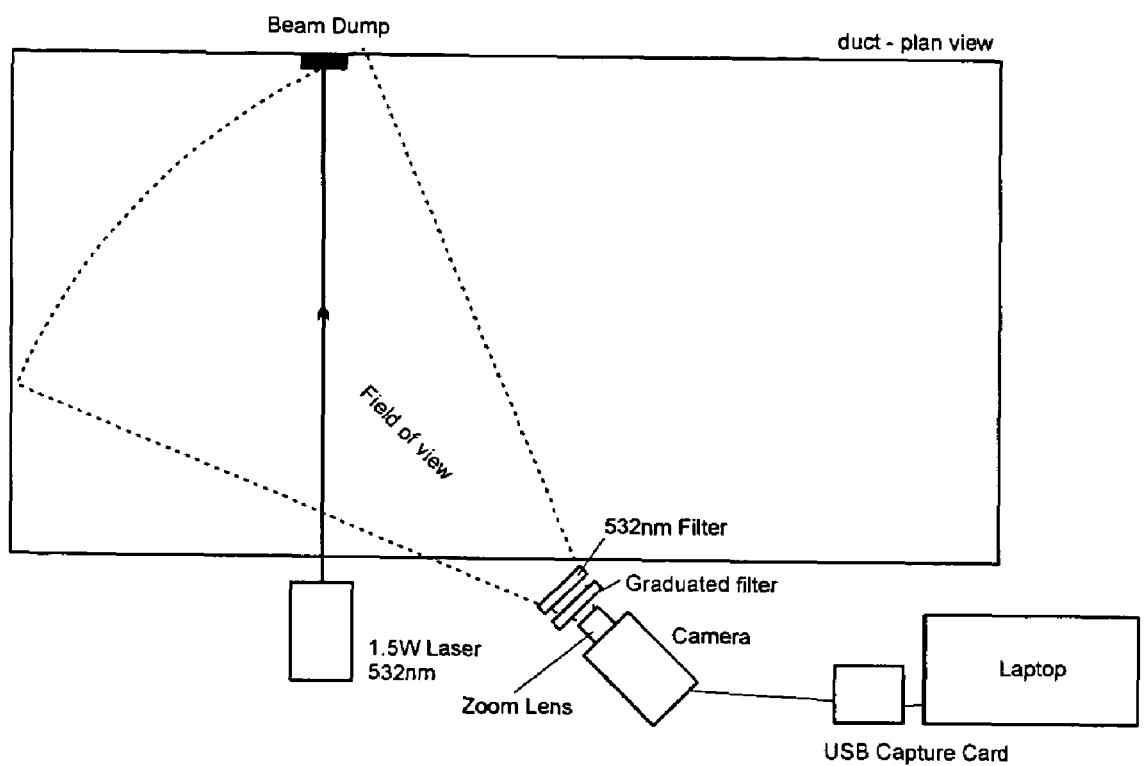
FIGS. 1, 2 and 3 are diagrammatic arrangements of an apparatus according to the invention.

FIG. 1 is a plan view of an apparatus according to the invention is shown diagrammatically in which illumination is provided from an emitter 2 which is a laser having output 1.5 W, a beam width of about 2 mm, at a wavelength of 532 nm (green). The beam is fanned, using a cylindrical lens, across a duct 4 from one wall at approximately right angles to the beam wall, 50% of the cross section of the duct being illuminated. At the opposite wall, a beam dump 6 is provided to absorb illumination received at that point so that essentially no emitted light is reflected back from that wall. Sparkles from any particulate in the duct are detected by a 0.08 Lux C/CS mount CCD camera 8 having a 12 mm lens having the centre of its field of view about at an angle of 45° across the duct. The camera is fitted with a zoom lens 10 to focus the field of view, and with a 532 nm filter 12 so as to accept only sparkles caused by light from the emitter, and with a graduated neutral density filter 14 (C41-960 variable density beamsplitter, Edmund Optics Ltd, York England) to aid normalisation of sparkles occurring close to the camera 8 with those distant from the camera 8. Both the emitter 2 and the camera are located outside the wall of the duct 4 so that illumination and sparkle are transmitted through the duct wall through transparent windows (not shown). Output from the camera 8 is then analysed using a laptop 16 so that required data on levels of particulate, e.g. identification and quantification of sparkles along the observed length, and any increase in levels with time can be calculated and monitored and any action re the particulate abatement system taken if required.

EXAMPLE 2

Figure 2:
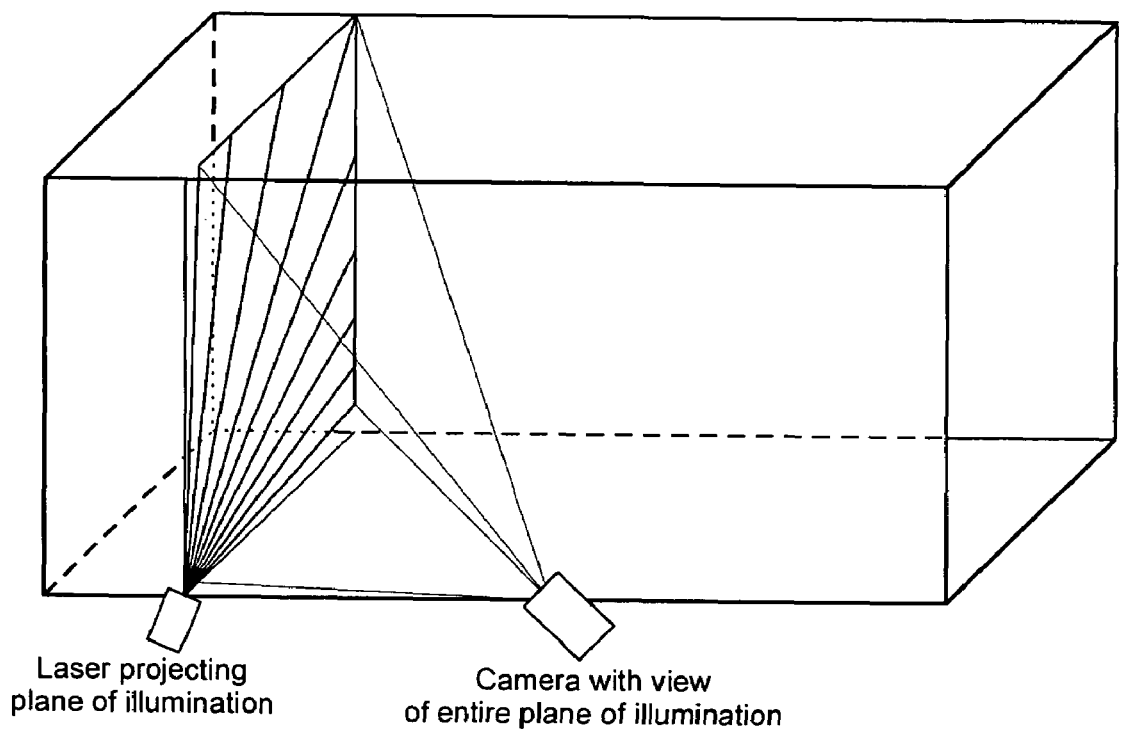

FIG. 2 is a 3-dimensional diagram of a illumination beam from the laser described in Example 1 in which the beam has been fanned using an optical lens across substantially the whole cross section of a duct; the emitter was positioned at a corner of the duct.

In a further embodiment of this apparatus, the beam from the laser is mechanically scanned using a stepper motor across substantially the whole cross section of the duct.

EXAMPLE 3

Figure 3:
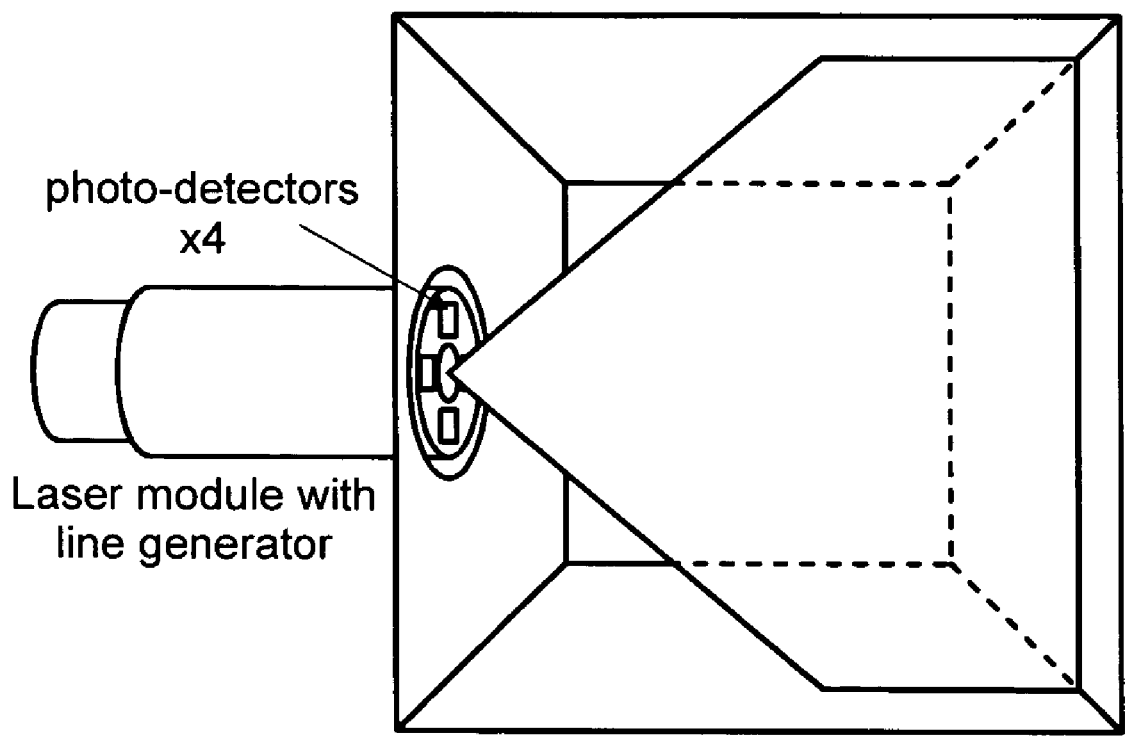
Figure 4:
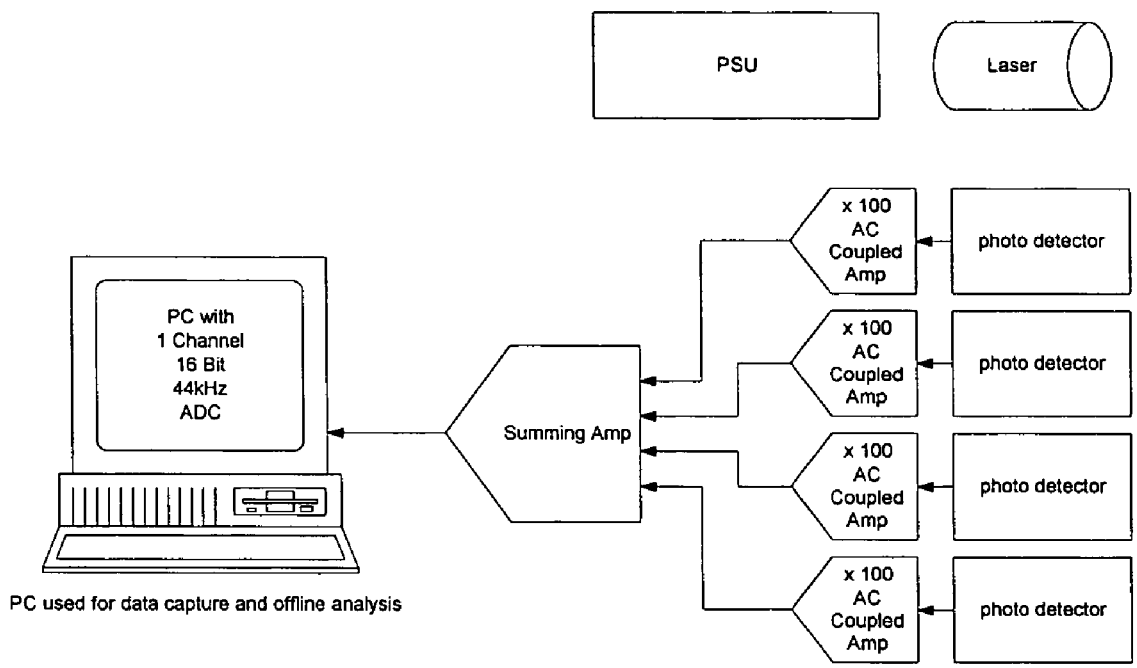
FIG. 4 shows a typical detector system for use in the apparatus of the invention.

FIGS. 3 and 4 show diagrammatically an apparatus according to the invention in which back scatter is detected using illumination from a laser emitter having 3 mW output at wavelength 680 nm. The apparatus is mounted at right angles to the direction of gas flow. The illumination from the laser emitter is fanned using an optical line generator which spreads (i.e. fans) the beam in one plane through 80° so that 60% of the cross sectional area of the duct is illuminated. Back scatter is detected using four phototransistors 18 arranged as a square around the emitter 2. The output from the phototransistors is then amplified using high gain AC-coupled amplifiers 20 and summing amp 22 so that any effects of ambient light (including varying changing ambient light) are minimised, and so that only transient sparkles from passing particulate are captured.

In this embodiment of the apparatus of the invention, the PC stores information received from the amplifiers, and then calculates the root mean square (RMS) of the amplitudes of that information to produce a figure for of particulate concentration across the illuminated area. Results of a number of RMS calculations are compared in Table 1 with "Alpha" (Trade Mark, Unidata Europe Limited, Sheffield, England) readings (a well established system which comprises a single path optical particulate beam monitor which records point to point measurements of particulate and then assumes that level uniformly over the whole area).

TABLE 1

| Reading No | Alpha Mg/m$^3$ | Back Scatter RMS |
|---|---|---|
| 1 | 13 | 78 |
| 2 | 25 | 85 |
| 3 | 13 | 80 |
| 4 | 14 | 82 |
| 5 | 7.6 | 80 |
| 6 | 390 | 1100 |
| 7 | 45 | 105 |
| 8 | 9 | 81 |
| 9 | 7.9 | 81 |
| 10 | 29 | 88 |
| 11 | 35 | 88 |

The results show that the apparatus is sensitive to passing particulate in the detectable range of the laser head. A large RMS reading shows a good correspondence to the large Alpha reading (test 6); in respect of the low Alpha readings, electrical and optical noise tended to distort the RMS reading, but more sophisticated electronics would remedy same. However the apparatus of preferred embodiments of the present invention advantageously detects and monitors particulate over a substantial portion of the duct.

EXAMPLE 4

Figure 5:
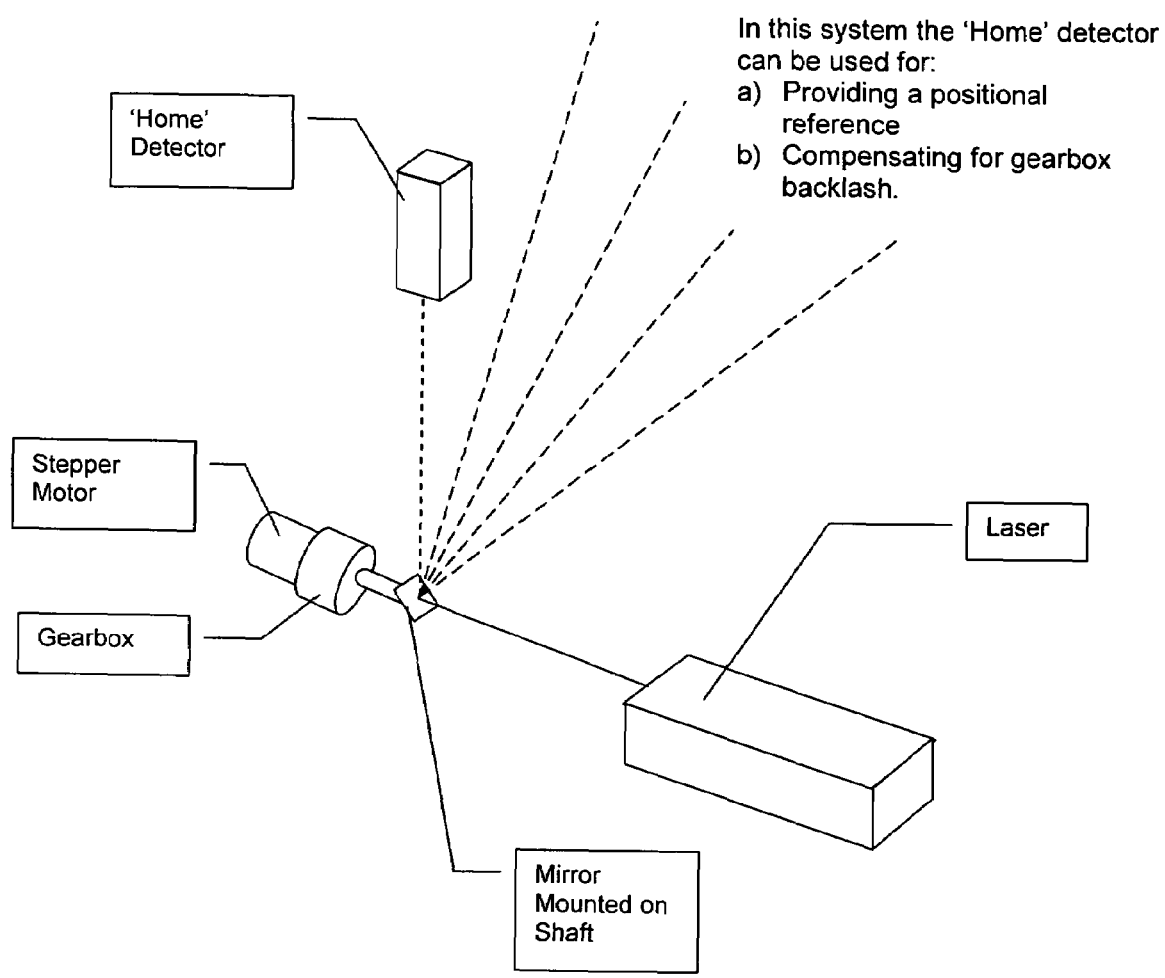
FIG. 5 shows a typical scanning arrangement.

FIG. 5 shows diagrammatically a scanning arrangement for use in the apparatus of the invention. In this arrangement, an illumination beam from the laser 2 is directed to a mirror 24 located on a shaft of a gearbox 26 from a stepper motor 28. The illumination from the mirror 24 may then be detected using detectors arranged as required. A "home detector" 25 may be used as a positional reference and for assisting in calculating any backlash in the gearbox 26.

A suitable stepper motor 28 has a step angle of 1.8° (Half step mode 0.9°), step angle accuracy 5%, voltage 5V; rated current 0.5 A/phase. A suitable gearbox 26 scans essentially the entire cross section of a duct; it is also has a ratio of 100:1 (step angle 0.0180/0.0090). Such a scanning arrangement is robust, vibration proof and capable being used over a wide temperature range, has low scan speed, repeatable positional information, and is easy to maintain.

EXAMPLE 5

In this Example, a series of experiments was carried out in one gantry of a filter house of a gas turbine electricity generating station, in which the apparatus of the invention was located in a duct upstream of the turbine in the gas inlet to the turbine. The gantry was about 15 m long and about 1 m wide. The apparatus was set up adjacent an array of filters in the gantry.

An apparatus similar to that in FIG. 3 and Example 3 except that the laser emitter had power between 200 mW and 1.6 W at a wavelength of 532 nm. The variable power allowed for rapid evaluation of the performance of the system over a wide range of optical power levels. The detector was a photodiode provided with a 35 mm-70 mm zoom lens, an optical band pass filter tuned to 532 nm, signal conditioners and amplifiers so that the signal could be fed to a digital oscilloscope and PC for storage of data. The detector system used is shown diagrammatically in FIG. 4.

Tests were carried out at various laser power outputs. Background signals were taken (i.e. with only ambient particulate present) and after introduction of particulate by sprinkling particulate into the monitored portion of the laser emitter beam.

Figure 6:
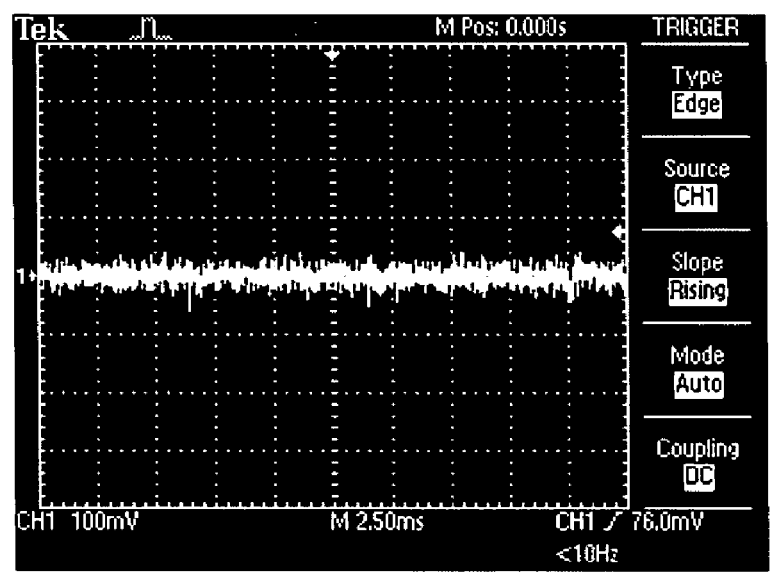
FIGS. 6 and 7 are oscilloscope traces from particulate using the apparatus of FIG. 3.
Figure 6:
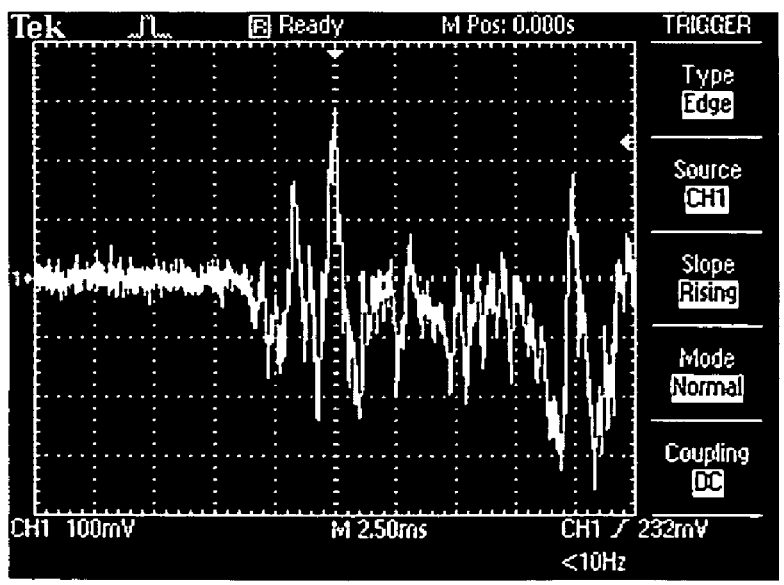

FIGS. 6a and 6b are oscilloscope traces at a laser power of 1.6 W, bias 5 μA, gain 23 from with background particulate (0.22 mg/m$^3$) and after introduction of particulate into the duct (9.74 mg/m$^3$) respectively.

Figure 7:
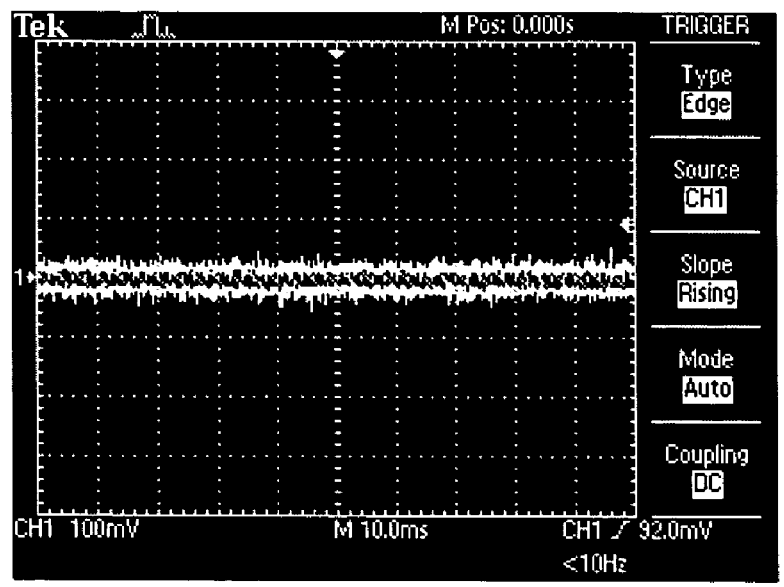
Figure 7:
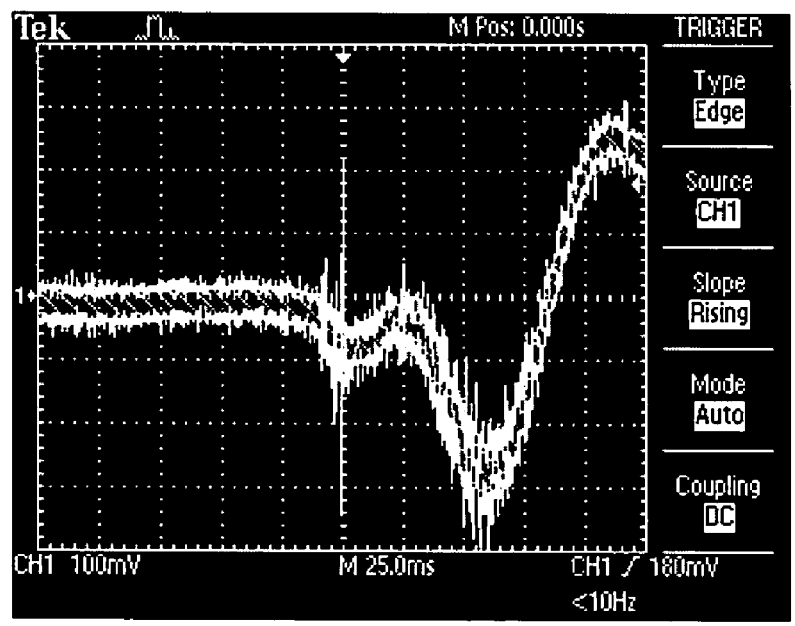

FIGS. 7a and 7b are oscilloscope traces at a laser power of 500 mW, bias 5 μA, gain 48 from with background particulate (0.22 mg/m$^3$) and after introduction of particulate (11.2 mg/m$^3$) respectively.

From FIG. 6b and FIG. 7b it can be seen that the presence of particulate is readily detected.

The invention claimed is:

1. An apparatus for detecting presence of transient particulate in gas within a duct, said apparatus comprising at least one emitter of illumination selected from infra-red, ultraviolet and visible radiation capable of being projected over essentially the entire cross section of the duct and at least one detector for detecting any sparkle of the illumination from the particulate.

2. An apparatus as in claim 1 in which the emitter of illumination is a single emitter.

3. An apparatus as in either claim 1 in which the illumination has a wavelength in the range 460 nm to 680 nm.

4. An apparatus as in claim 1 in which the emitter is a laser.

5. An apparatus as in claim 4 in which the illumination has a wavelength in the range 532 nm to 680 nm.

6. An apparatus as in claim 1 in which the detector is a camera.

7. An apparatus as in claim 1 in which the detector is at least one phototransistor.

8. An apparatus as in claim 1 in which the detector is a video camera.

9. An apparatus as in claim 1 in which the detectors are arranged around the illumination emitter.

10. An apparatus as in claim 1 in which the illumination from the emitter is fanned.

11. An apparatus as claimed in claim 10 in which the detector is fanned by a line generator.

12. An apparatus as claimed in claim 10 in which the illumination is fanned by an optical lens.

13. An apparatus as in claim 1 in which the illumination from the emitter is scanned.

14. An apparatus as in claim 13 in which the illumination from the emitter is scanned in the duct by a mirror, movement of which directs the illumination in the duct.

15. An apparatus as in claim 1 in which the emitter illumination frequency is matched to a detector specific for that frequency.

16. An apparatus as in claim 1 in which the emitter of illumination and the detector are located outside the duct wall, the duct wall being provided with transparent window so that illumination and sparkle are transmitted through the duct wall through transparent windows.

17. An apparatus for detecting particulate within a duct as claimed in claim 1 which also comprises a duct, located on which is at least one emitter of illumination capable of being projected over a substantial cross section of the duct and at least one detector for detecting any sparkle of the illumination from the particulate.

18. An apparatus as claimed in claim 17 which is located in the duct at the inlet to an industrial process.

19. An apparatus as claimed in claim 18 which the apparatus is located in the duct upstream of a turbine in the inlet to an industrial process having regard to the direction of the gas in the inlet.

20. An apparatus as claimed in claim 17 which is located in the duct at the outlet from an industrial process.

21. An apparatus as claimed in claim 20 which the apparatus is located in the duct downstream of a turbine in the outlet from an industrial process having regard to the direction of the gas in the outlet.

22. A method for detecting presence in gas of transient particulate above its normal zero or acceptable level within a duct which comprises subjecting a duct with at least one emitter of illumination selected from infra-red, ultraviolet and visible radiation, projecting the illumination over a substantial cross section of the duct and detecting any sparkle of the illumination from the particulate.

23. A method as claimed in claim 22 which comprises projecting the radiation in the duct at a position after the gas has been through an abatement system.

24. A method as claimed in claim 22 which comprises detecting transient particulate in a duct at the inlet to an industrial process.

25. A method as claimed in claim 24 in which the abatement system is in the inlet to an area requiring an essentially particulate free environment.

26. A method as claimed in claim 25 in which the essentially particulate free environment is in a hospital.

27. A method as claimed in claim 22 which comprises detecting transient particulate in a duct at the outlet from an industrial process.

28. A method as claimed in claim 27 which comprises detecting transient particulate in a duct upstream of a turbine in the inlet to an industrial process having regard to the direction of the gas in the outlet.

29. A method as claimed in claim 28 which comprises detecting transient particulate in a duct downstream of a turbine in the outlet from an industrial process having regard to the direction of the gas in the outlet.

30. A method as claimed in claim 29 in which the industrial process is an electricity generating station.

* * * * *